United States Patent [19]

Leboutet

[11] 4,426,351
[45] Jan. 17, 1984

[54] IRRADIATION HEAD FOR NEUTROTHERAPY APPARATUS

[75] Inventor: Hubert Leboutet, Buc, France

[73] Assignee: "C.G.R. MeV", Buc, France

[21] Appl. No.: 188,490

[22] Filed: Sep. 18, 1980

[30] Foreign Application Priority Data

Sep. 21, 1979 [FR] France .................. 79 23598

[51] Int. Cl.³ .................. G21K 5/10; A61N 5/10
[52] U.S. Cl. .................. 376/158; 378/206
[58] Field of Search .................. 128/653, 659, 1.1; 376/158; 378/205, 206

[56] References Cited

U.S. PATENT DOCUMENTS 4,075,497 2/1978 Kraus .................. 250/505

FOREIGN PATENT DOCUMENTS 1140448 7/1957 France .
1593516 7/1970 France .
2379294 9/1978 France .

OTHER PUBLICATIONS

Physics of Radiology, 3rd Ed., 2nd Printing, Charles C. Thomas Publisher, Springfield, Ill., (1969), Johns et al., pp. 103–113, 126–128.

*Primary Examiner*—Sal Cangialosi
*Attorney, Agent, or Firm*—Oblon, Fisher, Spivak, McClelland & Maier

[57] ABSTRACT

An irradiation head permitting the positioning of the area to be treated and the checking of this position. This irradiation head, which is disposed downstream of the neutron target, is provided which a turret carried by a supporting plate and which can rotate about an axis zz perpendicular to said plate. The supporting plate has a central opening A of axis ZZ coinciding with the axis of the useful neutron beam and the axis of the collimator. The turret has three openings $a_1$, $a_2$, $a_3$ which can successively face the opening A in accordance with the axis ZZ. Two of the openings $a_1$, $a_2$ are respectively associated with a light source $S_1$ and an X-ray source $S_2$ emitting beams of mean paths $f_1$ and $f_2$ equidistant with respect to axis zz, these beams being respectively designed for the positioning of the area to be treated and the checking of this position.

3 Claims, 4 Drawing Figures

IRRADIATION HEAD FOR NEUTROTHERAPY APPARATUS

BACKGROUND OF THE INVENTION

The present invention relates to a neutro-therapy apparatus utilizing a charged particle accelerator and more specifically relates to an irradiation head for this apparatus.

Certain neutrotherapy apparatus use charged particle accelerators of the linear accelerator type able to supply an electron beam accelerated to a few dozen MeV, or cyclotron-type accelerators for accelerating deuterons to between 15 and 35 MeV or protons to between 25 and 50 MeV.

These particle accelerators are generally associated with an isocentric irradiation device incorporating a movable arm which is able to rotate by 360° (or ±180°) about a horizontal axis. On the free end of this movable arm is provided an irradiation head which more particularly incorporates a target which is bombarded by the accelerated particle beam and as a result of the impact of this beam emits a neutron beam. A collimator associated with the target makes it possible to define a useful beam of neutrons from the neutrons emitted by the target.

An important operation in any use of irradiation apparatus, particularly in the case of medical irradiation apparatus is the positioning of the area to be irradiated relative to the irradiation beam.

Among the known positioning control means for the area to be treated reference is made to sensing head systems associated with a printing device which moves simultaneously with the sensing head and plots the contour of the area to be irradiated.

It is also known to use the irradiation beam as the positioning control means in X-ray apparatus. This beam is momentarily low energy regulated for controlling the position of the area to be treated.

SUMMARY OF THE INVENTION

The irradiation head of the neutrotherapy apparatus according to the invention incorporates a positioning and positioning checking systems for the area to be treated, the positioning operations being carried out and recorded prior to each treatment session.

The invention therefore relates to an irradiation head for a neutrotherapy apparatus incorporating a charged particle accelerator, a target able to emit neutrons under the impact of the accelerated charged particle beam and a collimator of axis ZZ defining a useful beam of neutrons, this irradiation head further comprising a source able to emit a light beam $f_1$, an other source able to emit an X-ray beam $f_2$ and means able to temporarily and successively position the beams $f_1$ and $f_2$ in accordance with the axis ZZ of the collimator, beam $f_1$ permitting the positioning of the area to be treated and beam $f_2$ the checking of this positioning.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
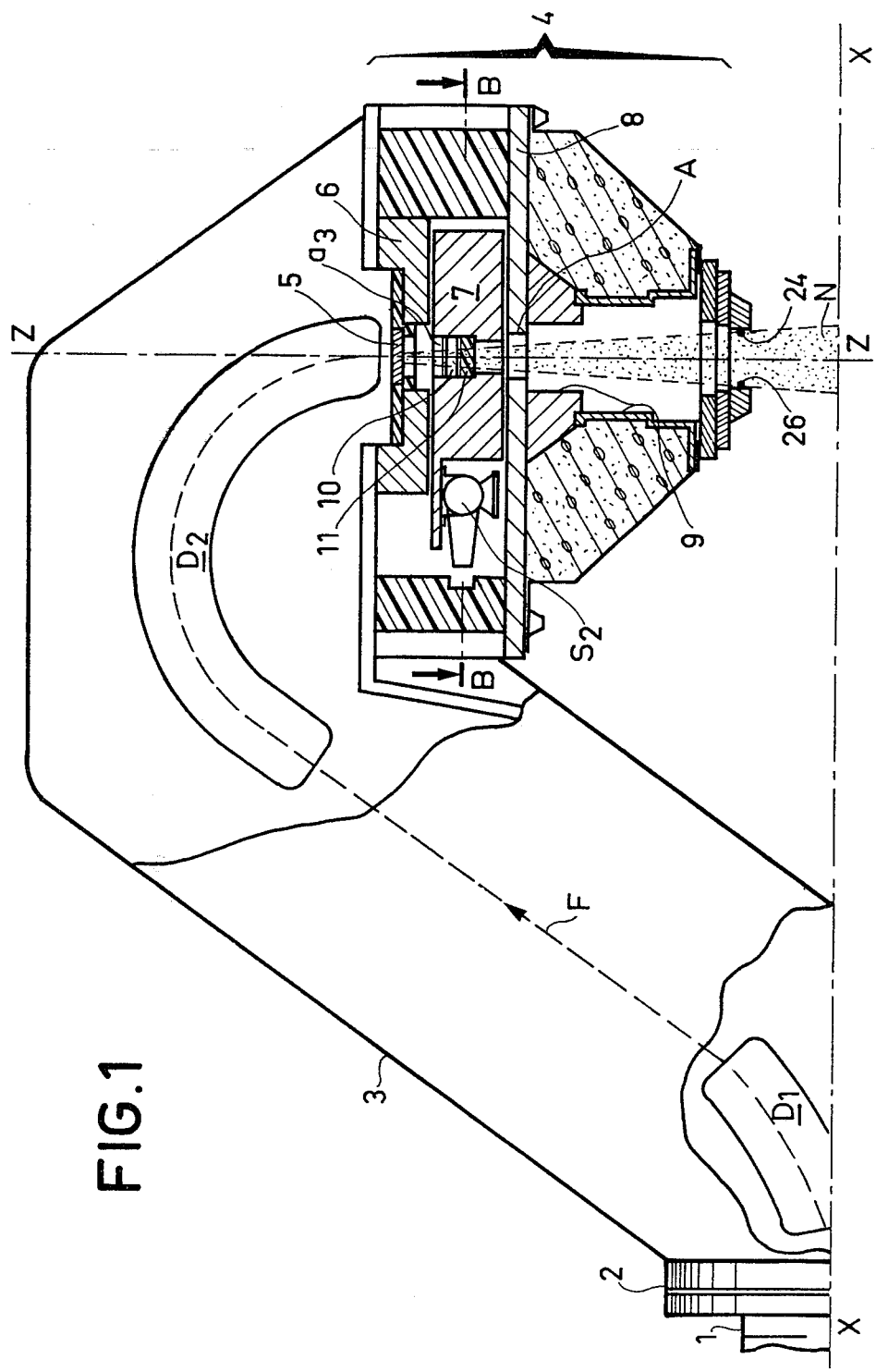
FIG. 1 a neutrotherapy apparatus equipped with an irradiation head according to the invention.

The neutrotherapy apparatus according to the invention shown in FIG. 1 incorporates a charged particle accelerator 1 and an isocentric movable arm 3 able to rotate by means of a roller bearing 2 about an axis XX coinciding with the mean path of the accelerated particles emerging from accelerator 1, an irradiation head 4 being placed on the free end of arm 3. Magnetic deviators $D_1$, . . . are placed in the movable arm 3 and make it possible to deviate the beam F of accelerated particles by a given angle $\theta$. Irradiation head 4 is provided with a target 5 able to emit neutrons under the impact of the accelerated particle beam F, a shield 6 defining a useful neutron beam N, a collimator system 9 of axis ZZ and known means for checking the characteristics of the useful neutron beam N.

In the irradiation head according to the invention is placed a turret 7 which moves around the axis ZZ. This turret 7 is carried by a support plate 8 having an opening A of axis ZZ via e.g. a ball bearing.

Figure 2:
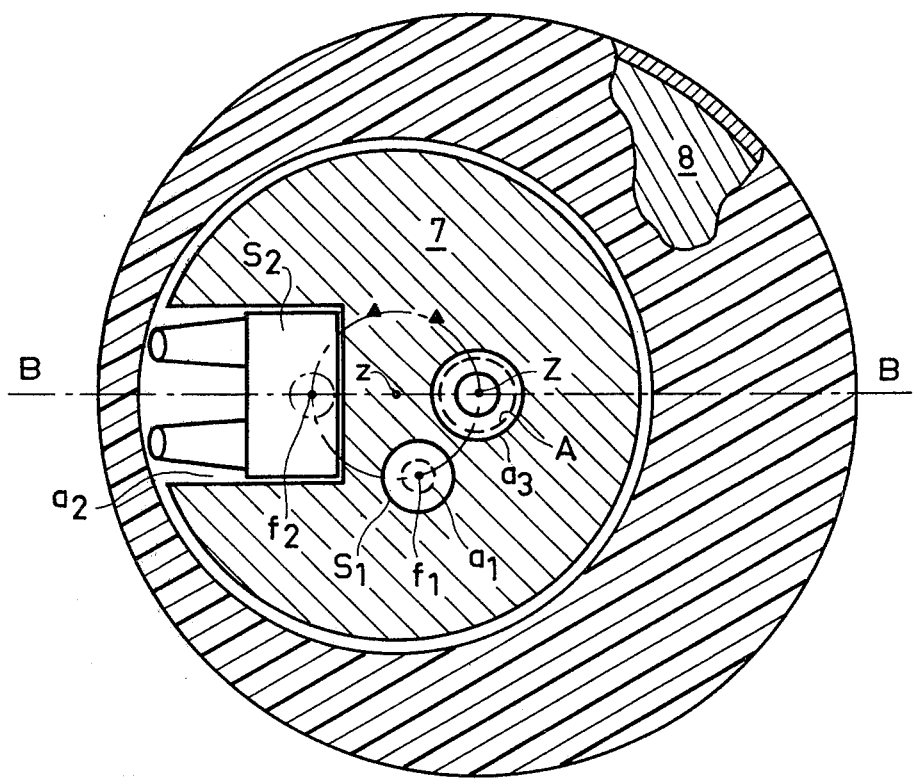
FIG. 2 a cross-section along BB of the irradiation head according to the invention.

As shown in FIG. 2, turret 7 has three openings $a_1$, $a_2$, $a_3$. With opening $a_1$ of turret 7 is associated a light source $S_1$ able to emit a light beam of mean path $f_1$ and with opening $a_2$ is associated an X-ray apparatus $S_2$ able to emit a beam of X-rays of mean path $f_2$. Sources $S_1$ and $S_2$ are positioned in such a way that the mean paths $f_1$ and $f_2$, which are substantially parallel to axis ZZ and respectively traverse openings $a_1$ and $a_2$, are equidistant from axis zz. Hereinafter, the light beam and X-rays beam are respectively referenced by their mean paths or trajectories $f_1$ and $f_2$.

The use of the radiotherapy apparatus according to the invention involves the following stages:

At first, the area to be treated is positioned relative to the axis ZZ of collimation system 9. This positioning is carried out by means of light beam $f_1$ which, in the plane of the area to be treated, defines the latter. The turret 7 is rotated about axis 22 until opening 91 is aligned with axis 22. The size of the light spot supplied by beam $f_1$ is determined by means of collimation system 9, whereby said beam $f_1$ emitted by source $S_1$ has successively passed through opening $a_1$ of the turret 7 and opening A of the support plate 8, these openings $a_1$ and A facing each other.

Then, this positioning operation is followed by the checking of the positioning of the area to be treated by means of X-ray beam $f_2$ emitted by source $S_2$. The mean path of beam $f_2$ is made to coincide with axis ZZ by a second rotation of turret 7 around axis zz. When source $S_2$ is operating, it is able to take an X-ray picture (or carry out fluoroscopy) of the area to be treated and thus check its correct positioning with respect to axis ZZ of collimator 9.

Finally, by a final rotation of turret 7, the axis of orifice $a_3$, permitting the passage of irradiation beam N, is placed in accordance with the axis ZZ.

When this third rotation has been performed a safety system associated with turret 7 is automatically or manually unlocked, so that accelerator 1 can be started up, followed by the irradiation by the useful neutron beam N of the area to be treated. The useful neutron beam N of the target 5 successively traverses openings $a_3$ of turret 7 and A of the supporting plate 8, as well as collimator 9.

Orifice $a_3$ can contain ionization chambers 10 (FIG. 1) permitting the control of the characteristics of irradiation beam N (in particular the dose rate). A known filter 11, e.g. of polyethylene can be placed in accordance with the axis of orifice $a_3$ upstream of ionization chambers 10. This filter is designed for the neutron beam N and eliminates the neutrons with too low an energy.

However, it is pointed out that the (not shown) X-ray target of X-ray source $S_2$, due to the construction of the irradiation head, is placed downstream of the neutron beam-emitting target 5, because the latter is carried by the vacuum enclosure of the irradiation head and cannot move. Thus, the surface of the area irradiated by X-ray beam $S_2$ is slightly larger than the surface of the area irradiated by neutron beam N.

Figure 4:
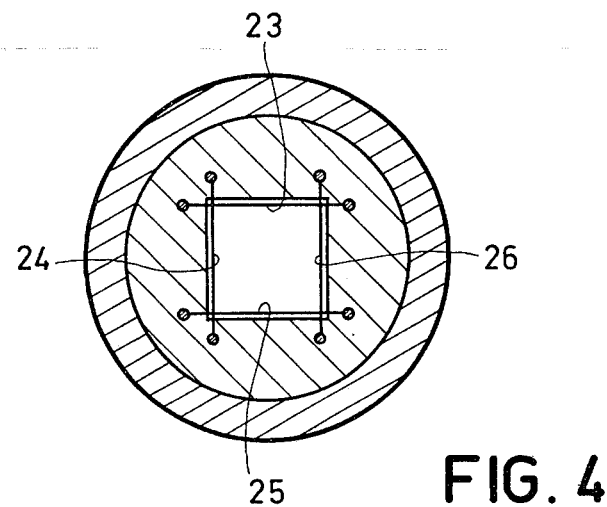
FIGS. 3 and 4 respectively a collimator used in the irradiation head according to the invention and a detail of said collimator.
Figure 3:
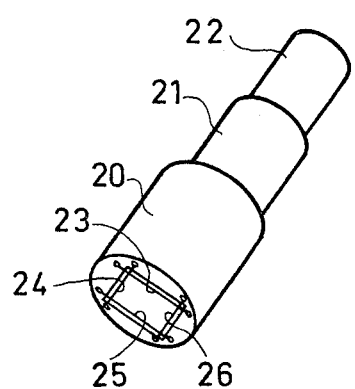

In order to obtain a precise definition of the area to be treated, collimator 9 of the irradiation head according to the invention can have, in the manner shown in FIGS. 3 and 4, a cylindrical detachable system of elements 20, 21, 22, whose frustum-shaped axial opening can have at its free end a shield with a square or rectangular opening, whose inner periphery is provided with lead wires 23, 24, 25, 26 which are slightly set back therefrom. These wires are positioned in such a way that the projection of the wires onto the X-ray-sensitive film located in the plane of the area to be treated precisely displays the field which will be exposed to a useful neutron beam N.

What is claimed as new and desired to be secured by Letters Patent of the United States is:

1. An irradiation head for a neurotherapy apparatus comprising:

means in said head for emitting an irradiating beam along a first axis, said means for emitting comprising (a) a charged particle accelerator means for emitting a beam of charged particles, (b) a fixed first target in the path of said charged particle beam, said target being constructed and adapted to emit an irradiating beam of neutrons along said first axis, under the impact of said charged particles, and (c) collimator means along said first axis and in the path of said irradiating beam for focusing said irradiating beam;

positioning means in said head for positioning a second target relative to said beam, said positioning means comprising (a) a turret positioned between said first target and said collimator, said turret being rotatable about a second axis parallel to said first axis, whereby selected portions of said turret intercept said first axis during rotation of said turret about said second axis, (b) light emitting means mounted in one of said selected portions of said turret for emitting a light beam along said first axis, (c) an X-ray source mounted in a second of said selected portions of said turret for emitting an X-ray beam along said first axis, said X-ray source being independent of said charged particle beam, and (d) means for rotating said turret, whereby said light emitting means and said X-ray source is sequentially and selectively be positioned along said first axis for providing both visual and X-ray positioning of said second target relative to said irradiating beam.

2. The irradiation head of claim 1 including irradiating beam passage means in a third of said selected portions of said turret for permitting passage of said irradiating beam, said passage means including ionization chambers for controlling the characteristics of said irradiating beam.

3. The irradiation head of claim 1 including means for removably positioning a plurality of wires in said collimator and along said first axis, said wires being located so as to define the limits of said irradiating beam on said second target, when said wires are traversed by said X-ray beam.

* * * * *